United States Patent
Robvieux et al.

(10) Patent No.: US 10,370,616 B2
(45) Date of Patent: Aug. 6, 2019

(54) ALCOHOL WITH FLORAL ODOR

(71) Applicant: FIRMENICH SA, Geneva 8 (CH)

(72) Inventors: Fabrice Robvieux, Geneva (CH); Pierre-Alain Blanc, Crans-Montana (CH)

(73) Assignee: FIRMENICH SA, Geneva (CH)

( * ) Notice: Subject to any disclaimer, the term of this patent is extended or adjusted under 35 U.S.C. 154(b) by 0 days.

(21) Appl. No.: 15/962,585

(22) Filed: Apr. 25, 2018

(65) Prior Publication Data

US 2018/0237725 A1    Aug. 23, 2018

Related U.S. Application Data

(62) Division of application No. 15/034,712, filed as application No. PCT/EP2014/072217 on Oct. 16, 2014, now Pat. No. 9,982,218.

(30) Foreign Application Priority Data

Nov. 8, 2013   (EP) .................................... 13192085

(51) Int. Cl.
| | | |
|---|---|---|
| A61K 8/34 | (2006.01) | |
| A61Q 5/02 | (2006.01) | |
| A61Q 5/06 | (2006.01) | |
| A61Q 15/00 | (2006.01) | |
| A61Q 19/10 | (2006.01) | |
| C11D 3/20 | (2006.01) | |
| C11D 3/50 | (2006.01) | |
| C11B 9/00 | (2006.01) | |

(52) U.S. Cl.
CPC .............. *C11B 9/0061* (2013.01); *A61K 8/34* (2013.01); *A61Q 5/02* (2013.01); *A61Q 5/06* (2013.01); *A61Q 15/00* (2013.01); *A61Q 19/10* (2013.01); *C11D 3/2034* (2013.01); *C11D 3/50* (2013.01)

(58) Field of Classification Search
None
See application file for complete search history.

(56) References Cited

FOREIGN PATENT DOCUMENTS

| | | |
|---|---|---|
| DE | 20 51 319 A1 | 4/1974 |
| EP | 1 780 258 A1 | 5/2007 |
| WO | 2005/004601 A1 | 1/2005 |
| WO | 2008/054067 A1 | 5/2008 |
| WO | WO-2008054067 A1 * | 5/2008 .............. C11B 9/00 |

OTHER PUBLICATIONS

C.S. Sell. Angew. Chem. Int. Ed.2006, 45, pp. 6254-6261. (Year: 2006).*
STIC Search Results for claimed structures. (Year: 2017).*
International Search Report and Written Opinion, Appl. No. PCT/EP2014/072217 dated Feb. 16, 2015.
S. Arctander, "2200: 3-Methyl-5-Phenylpentanol-1"; "2575: Phenyl Heptyl Alcohol," Perfume and Flavor Chemicals (Aroma Chemicals) II, Montclair, NJ, USA (1969), 10 pages.
Fischli et al., "Cob(I)alamin als Katalysator, 5. Mitteilung [1]. Enantioselektive Reduktion α,β-ungesättigter Carbonylderivate," Helvetica Chimica Acta, 62(7):2361-2737 (1979).
Köbrich et al., "Konjugierte Verbindungen, II. Ringspaltung von Pyryliumsalzen mit metallorganischen Verbindungen," Justus Liebigs Ann Chem 654, 131-145 (1962).
Sell, "On the Unpredictability of Odor," Angew. Chem. Int. Ed., 45:6254-6261 (2006).
U.S. Appl. No. 15/034,712, Restriction Requirement dated Feb. 23, 2017.
U.S. Appl. No. 15/034,712, Non-Final Rejection dated Jul. 27, 2017.
U.S. Appl. No. 15/034,712, Notice of Allowance dated Feb. 8, 2018.

* cited by examiner

*Primary Examiner* — Michael P Cohen
(74) *Attorney, Agent, or Firm* — Winston & Strawn LLP

(57) ABSTRACT

The present invention relates to perfuming compositions and consumer products that contain compounds of formula

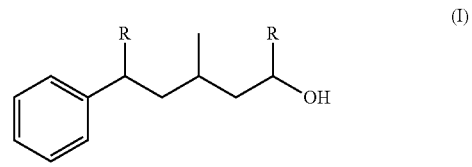

(I)

in the form of any one of its stereoisomers or a mixture thereof and wherein one R represents a methyl group and the other R is a hydrogen atom. The compounds are useful as perfuming ingredients in particular to impart lily of the valley/gardenia odor notes to the composition or product.

8 Claims, No Drawings

ALCOHOL WITH FLORAL ODOR

CROSS-REFERENCE TO RELATED APPLICATIONS

This application is a division of U.S. application Ser. No. 15/034,712 filed May 5, 2016, which is the 371 of International Patent Application PCT/EP2014/072217 filed Oct. 16, 2014, which claims the benefit of European patent application no. 13192085.2 filed Nov. 8, 2013.

TECHNICAL FIELD

The present invention relates to the field of perfumery. More particularly, it concerns the use as perfuming ingredient of compounds of formula (I) as defined below, which are useful perfuming ingredients of the lily of the valley/gardenia type. Therefore, following what is mentioned herein, the present invention comprises the invention's compounds as part of a perfuming composition or of a perfuming consumer product.

PRIOR ART

To the best of our knowledge, 3-methyl-5-phenylhexan-1-ol was never disclosed and 4-methyl-6-phenylhexan-2-ol is mentioned only in one document. In said document, *Helv. Chim. Acta* 1979, 62 (7), 2361-2373, the compound of formula (I) is synthesized by reduction using Cobalt. However, this prior art document does not report or suggest any organoleptic properties of the compounds of formula (I), or any use of said compounds in the field of perfumery.

To the best of our knowledge, the closest analogue known in the perfumery is the chemical 3-methyl-5-phenylpentanol also known as phenyhexanol and reported in the book by S. Arctander as n° 2200 (Perfume and Flavor Chemicals, 1969, Montclair, N.J., USA). We may also cite 6-phenylheptan-2-ol reported in the book by S. Arctander n° 2575 (Perfume and Flavor Chemicals, 1969, Montclair, N.J., USA), 2-methyl-5-phenylpentan-1-ol (known as Rosaphen®; origin Symrise AG, Germany) and 4-methyl-6-phenylheptan-2-ol described in *Justus Liebigs Ann. Chem.* 1962, 654, 131-145. However, among the known derivatives of 5-phenylpentanol, the ones with a primary alcohol and one methyl group as 3-methyl-5-phenylpentanol or as Rosaphen® are reported as having a rosy note; and the ones with a secondary alcohol and two or three methyl groups as 6-phenylheptan-2-ol or 4-methyl-6-phenylheptan-2-ol show a rosy or rhubarb note type. In other words, quite different notes are reported for the prior art compare with the present invention's compounds.

These prior art documents do not report or suggest any organoleptic properties of the compounds of formula (I) and do not report or suggest any use of said compounds in the field of perfumery.

DESCRIPTION OF THE INVENTION

We have now surprisingly discovered that a compound of formula

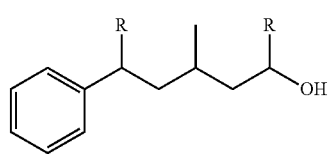

(I)

in the form of any one of its stereoisomers or a mixture thereof and wherein one R represents a methyl group and the other R is a hydrogen atom;

can be used as perfuming ingredient, for instance to impart odor notes of the lily of the valley/gardenia.

For the sake of clarity, by the expression "any one of its stereoisomers", or the similar, it is meant the normal meaning understood by a person skilled in the art, i.e. that the invention's compound can be a pure enantiomer or diastereoisomer. Indeed, the compounds of formula (I) have two stereogenic centers which can have different stereochemistry (i.e. compound (I) can have (R,R) or (R,S) configuration). Each of said stereogenic centers can be in a relative configuration R or S or a mixture thereof or in other words said compound of formula (I) can be in a form of pure enantiomer or distereoisomer, or in a form of a mixture of stereoisomers.

As prefered examples of the invention's compounds, one may cite, 4-methyl-6-phenylhexan-2-ol, which possesses an odor characterized by a lily of the valley/gardenia and green notes with honey aspect. This compound is very powerful in application and the floral note of this ingredient is significantly more substantive than the known compounds with the same kind of floral note, such as styrallyl acetate. Its organoleptic character differentiates from the phenylhexanol by having green connotation without rosy note and by its power. According to a particular embodiment of the invention, compound of formula (I) is in the form of a mixture of stereoisomers containing at least 80% of both stereoisomers (2RS,4RS)-4-methyl-6-phenylhexan-2-ol and (2SR,4RS)-4-methyl-6-phenylhexan-2-ol. Preferably compound of formula (I) is in the form of a mixture of stereoisomers containing at least 50% of (2RS,4RS)-4-methyl-6-phenylhexan-2-ol. For the sake of clarity, by the expression "2RS, 4RS" it is meant an equimolar mixture of 2R,4R and 2S,4S and by the expression "2SR,4RS" it is meant an equimolar mixture of 2S,4R and 2R,4S.

As other example, one may cite 3-methyl-5-phenylhexan-1-ol, which possesses an odor similar to the one mentioned above but distinguishing itself by having a stronger gardenia/styrallyle note as well as a bit weaker green note and less clear.

TABLE 1

Invention's compounds and its odor properties and prior art compounds

| Compound structure and name | Odor notes |
|---|---|
| rac-4-methyl-6-phenylhexan-2-ol | Lily of the valley/gardenia and green notes with honey aspect<br>No rosy note |
| rac-3-methyl-5-phenylhexan-1-ol | Lily of the valley/gardenia<br>No rosy note |
| Prior art compounds | |
| 3-methyl-5-phenylpentanol | Rosy note |

TABLE 1-continued

Invention's compounds and its odor properties and prior art compounds

| Compound structure and name | Odor notes |
|---|---|
| (structure) 6-phenylheptan-2-ol | Rose-blossom note and with somewhat geraniol |
| (structure) [unnamed, shown above 6-phenylheptan-2-ol label] | Oily-rosy and delicately green note |
| (structure) 4-methyl-6-phenylheptan-2-ol | Rhubarb note slightly floral No gardenia note |

When the odor of the invention's compounds is compared with that of the prior art compounds, then the invention's compounds distinguish themselves by a clearly gardenia/lily of the valley note and by lacking the rosy note characteristic of phenylhexanol or 6-phenylheptan-2-ol. Furthermore, the rhubarb note reported for 4-methyl-6-phenylheptan-2-ol is weaker for the invention's compound. Said differences lend the invention's compounds and the prior art compounds to be each suitable for different uses, i.e. to impart different organoleptic impressions.

As mentioned above, the invention concerns the use of a compound of formula (I) as perfuming ingredient. In other words, it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any composition containing a compound (I) and which can be advantageously employed in perfumery industry.

Said compositions, which in fact can be advantageously employed as perfuming ingredients, are also an object of the present invention.

Therefore, another object of the present invention is a perfuming composition comprising:
i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e., that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

As solid carriers one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualitat, Behr's Verlag GmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation technique.

By "perfumery base" we mean here a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor. The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for his work.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery. Thus, unpurified reaction mixtures are generally excluded from the present invention unless otherwise specified.

Furthermore, the invention's compound can also be advantageously used in all the fields of modern perfumery, i.e. fine or functional perfumery, to positively impart or modify the odor of a consumer product into which said compound (I) is added. Consequently, another object of the present invention is represented by a perfuming consumer product comprising, as perfuming ingredient, at least one compound of formula (I), as defined above.

The invention's compound can be added as such or as part of an invention's perfuming composition.

For the sake of clarity, it has to be mentioned that, by "perfuming consumer product" it is meant a consumer product which is expected to deliver at least a pleasant perfuming effect to the surface to which it is applied (e.g. skin, hair, textile, or home surface). In other words, a perfuming consumer product according to the invention is a perfumed consumer product which comprises the functional formulation, as well as optionally additional benefit agents, corresponding to the desired consumer product, e.g. a detergent or an air freshener, and an olfactive effective amount of at least one invention's compound. For the sake of clarity, said perfuming consumer product is a non-edible product.

The nature and type of the constituents of the perfumery consumer product do not warrant a more detailed description here, which in any case would not be exhaustive, the skilled person being able to select them on the basis of his general knowledge and according to the nature and the desired effect of said product.

Non-limiting examples of suitable perfumery consumer product can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent.

Some of the above-mentioned consumer products may represent an aggressive medium for the invention's compound, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.001% to 10% by weight, or even more, of the compounds of the invention based on the weight of the composition into which they are incorporated. Concentrations lower than these, such as in the order of 0.01% to 5% by weight, can be used when these compounds are incorporated into perfumed articles, percentage being relative to the weight of the article.

The invention's compounds can be prepared according to a method reported in the literature or standard methods known in the art as described herein below.

EXAMPLES

The invention will now be described in further details by way of the following examples, wherein the abbreviations have the usual meaning in the art, the temperatures are indicated in degrees centigrade (° C.) ; the NMR spectral data were recorded in $CDCl_3$ (if not stated otherwise) with a 360 or 400 MHz machine for $^1H$ and $^{13}C$, the chemical shifts ☐ are indicated in ppm with respect to TMS as standard, the coupling constants J are expressed in Hz.

Example 1

Synthesis of Compounds of Formula (I)

a) 4-methyl-6-phenylhexan-2-ol i) To 98 mL of heptane was added benzaldehyde (100 g, 0.94 mol), camphorsulfonic acid (0.26 g, 0.001 mol) dissolved in 0.3 g of water. The mixture was heated to a pot temperature of 98-100° C. Remove any water in the flask as a water/heptane azeotrope (78° C. boiling point). When the flask temperature has stabilized, begin the addition of methylisoprenol (73.6 g, 0.74 mol). Approximately 13.2 g of water will be removed azeotropically during the reaction. Let the reaction continue until water removal has stopped. This will be indicated by a 20° C. rise in the vapor temperature at the top of the column. Slowly add 0.4 g sodium carbonate dissolved in 8 g of water to the flask. Check to make sure the pH is above 9. The two layers were separated and the aqueous phase extracted with 100 ml of ether. The two ethereal phases were combined, washed with 50 ml of water and 50 ml of brine and dried over $Na_2SO_4$. Filtration and concentration gave 161 g of oil. This oil was purified by vacuum distillation (68 to 100° C., 0.5 to 0.05 mbar) through a short path to give 100.5 g (61%) of a mixture of double bond isomers of 2-methyl-4-methylene-6-phenyltetrahydro-2H-pyran.

$^1H$ NMR (400 MHz, $CDCl_3$): 7.40-7.36 (m, 2H), 7.35-7.30 (m, 2H), 7.27-7.22 (m, 1H), 4.78 (m, 2H), 4.32 (dd, J=2.3 Hz, 0.5 Hz, 1H), 3.58 (m, 1H), 2.42 (dt, J =2.7 Hz, 0.4 Hz, 1H), 2.24 (m, 2H), 2.03 (m, 1H), 1.30 (d, J=1.2 Hz, 3H).

¹³C NMR (100 MHz, CDCl₃): 22.0 (q), 42.3 (t), 42.7 (t), 74.9 (d), 80.4 (d), 108.6 (t), 125.9 (d), 127.5 (d), 128.4 (d), 142.6 (s), 144.8 (s).

ii) To the mixture obtained in previous step (15 g, 0.079 mol) in the autoclave was added Pd/C 5% (ESCAT 11, 50% wet). Pressurize to 13 bar with H₂ and begin heating to 120° C. After hydrogenation of the olefin, the autoclave was vented off. pTsOH.H₂O (0.021 g, 0.001 mol) in 0.5 ml of water was added. After the p-toluenesulfonic acid has been added, pressurize back to 13 bar with H₂, raise the set point temperature to 140° C., and continue the hydrogenation reaction for another 3 hours. Analyze by G.C. When the hydrogenation is complete, cool the autoclave to RT and then vent to atmospheric pressure. Pressure the autoclave with 2.5 bar of N₂ and vent again to atmospheric pressure to purge residual Hz. Repeat this purge and vent again. The mixture was filtered over Celite®, washed with 50 ml of saturated NaHCO₃ solution, washed with 50 ml of brine. The organic phase was dried over Na₂SO₄. Filtration and concentration gave 13.5 g of oil. This oil was purified by vacuum distillation (100 to 150° C., 0.5 to 0.02 mbar) through a short path to give 13.2 g (87%) of 4-methyl-6-phenylhexan-2-ol as a mixture of diastereoisomers with the ratio 94/6 ((2RS,4RS)/(2SR,4RS)).

(2RS,4RS)-4-methyl-6-phenylhexan-2-ol

¹H NMR (400 MHz, CDCl₃): 7.33-7.22 (m, 2H), 7.22-7.12 (m, 3H), 4.02-3.83 (m, 1H), 2.71-2.63 (m, 1H), 2.62-2.54 (m, 1H), 1.75-1.44 (m, 4H), 1.41-1.32 (m, 1H), 1.25-1.20 (m, 1H), 1.18 (d, JHH=4.9 Hz, 3H), 0.97 (d, JHH=5.2 Hz, 3H).

¹³C NMR (100 MHz, CDCl₃): 142.9 (s), 128.3 (d), 125.6 (d), 65.7 (d), 46.7 (d), 39.5 (t), 33.3 (t), 29.2 (t), 24.3 (q), 19.3 (q).

(2SR,4RS)-4-methyl-6-phenylhexan-2-ol

¹H NMR (400 MHz, CDCl₃): 7.30-7.24 (m, 2H), 7.21-7.15 (m, 3H), 3.96-3.84 (m, 1H), 2.73-2.63 (m, 1H), 2.62-2.52 (m, 1H), 1.75-1.66 (m, 1H), 1.65-1.57 (m, 1H), 1.49-1.36 (m, 3H), 1.29-1.20 (m, 1H), 1.16 (d, JHH=4.1 Hz, 3H), 0.98 (d, JHH=4.4 Hz, 3H).

¹³C NMR (100 MHz, CDCl₃): 142.9 (s), 128.3 (d), 125.7 (d), 66.2 (d), 46.8 (t), 38.8 (t), 33.3 (t), 29.6 (d), 23.8 (q), 20.1 (q).

b) 3-methyl-5-phenylhexan-1-ol i) A mixture of toluene (500 ml), acetophenone (120 g, 1 mole), isoprenol (129 g, 1.5 mol) and para-toluene sulfonic acid (3 g, 0.02 mol) was heated under reflux 4 h until complete removal of water. The reaction mixture was cooled to RT and filtered over Al₂O₃. Volatiles were evaporated and the crude mixture was purified by chromatography (hexane/ethyl acetate 9/1) following by distillation afforded 102 g of a mixture of double bond isomers of 2-methyl-2-phenyl-4-methylene-tetrahydropyrane (54%).

ii) To compounds obtained in previous step (10 g, 0.053 mol) in the autoclave was added Pd/C 5% (500 mg). Pressurize to 13 bar with H₂ and begin heating to 120° C. After hydrogenation of the olefin, the autoclave was vented off. HCl (2 ml) was added. After the HCl has been added, pressurize back to 13 bar with Hz, raise the set point temperature to 140° C., and continue the hydrogenation reaction for another 3 hours. Analyze by G.C. When the hydrogenation is complete, cool the autoclave to RT and then vent to atmospheric pressure. Pressure the autoclave with 2.5 bar of Na and vent again to atmospheric pressure to purge residual Hz. Repeat this purge and vent again. The mixture was filtered over Celite®, washed with 50 ml of saturated NaHCO₃ solution, washed with 50 ml of brine. The organic phase was dried over Na₂SO₄. Filtration and concentration gave an oil which was purified by chromatography and distillation to give 4.7 g (46%) of 3-methyl-5-phenylhexan-1-ol.

¹³C NMR (100 MHz, CDCl₃): 21.3, 21.4, 26.3, 36.3, 40.1, 43.4, 60.3, 125.9, 128.1, 128.5, 147.7.

Example 2

Preparation of a Perfuming Composition

A perfuming composition for detergent was prepared by admixing the following ingredients:

| Parts by weight | Ingredient |
|---|---|
| 400 | Isobornyl Acetate |
| 200 | Benzyl Acetate |
| 100 | Phenylethyl Acetate |
| 800 | Verdyl Acetate |
| 20 | 2-methylundecanal |
| 50 | Cetalox ®[1] |
| 400 | Citronellol |
| 20 | Coumarine |
| 40 | Allyl Cyclohexylpropionate |
| 150 | (1'R,E)-2-ethyl-4-(2',2',3'-trimethyl-3'-cyclopenten-1'-yl)-2-buten-1-ol |
| 800 | Dihydromyrcenol |
| 300 | Eugenol |
| 300 | (+−)-(1-Ethoxyethoxy)cyclododecane |
| 200 | Gamma Undecalactone |
| 300 | Geraniol 60 |
| 500 | Habanolide ®[2] |
| 20 | Hivernal ® Neo[3] |
| 1000 | Iso E ® Super[4] |
| 40 | Isoeugenol Extra |
| 1000 | Isoraldeine 70 P |
| 280 | Linalool |
| 100 | Crystal moss |
| 400 | Hedione ®[5] |
| 40 | Nirvanol ®[6] |
| 20 | Oxyde de Rose |
| 400 | Verdyl Propionate |
| 600 | Benzyl Salicylate |
| 40 | Cis-3-Hexenol Salicylate |
| 400 | Salicynile ®[7] |
| 100 | Orange Oil |
| 150 | Undecavertol ®[8] |
| 800 | Verdox ®[9] |
| 30 | 10%* Violettyne |
| 10000 | |

*in isopropyl myristate
[1] dodecahydro-3a,6,6,9a-tetramethyl-naphtho[2,1-b]furan; origin: Firmenich SA, Geneva, Switzerland
[2] pentadecenolide; origin: Firmenich SA, Geneva, Switzerland
[3] 3-(3,3/1,1-dimethyl-5-indanyl)propanal; origin: Firmenich SA, Geneva, Switzerland
[4] 1-(octahydro-2,3,8,8-tetramethyl-2-naphthalenyl)-1-ethanone; origin: International Flavors & Fragrances, USA
[5] methyl dihydrojasmonate; origin: Firmenich SA, Geneva, Switzerland
[6] 3,3-dimethyl-5-(2,2,3-trimethyl-3-cyclopenten-1-yl)-4-penten-2-ol; origin: Firmenich SA, Geneva, Switzerland
[7] (2Z)-2-Pnenyl-2-hexenitrile; origin: Firmenich SA, Geneva, Switzerland
[8] 4-methyl-3-decen-5-ol; origin: Givaudan SA, Vernier, Switzerland
[9] 2-tert-butyl-1-cyclohexyl acetate; origin: International Flavors & Fragrances, USA The addition of 500 parts by weight of 4-methyl-6-phenylhexan-2-ol to the above-described composition imparted to the latter an overall connotation in the direction of gardenia/lily of the valley. The addition of the same amount of the prior art phenylhenanol provided totally different results which is clearly a rosy note.

Example 3

Preparation of a Perfuming Composition

A perfuming composition for air freshener was prepared by admixing the following ingredients:

| Parts by weight | Ingredient |
| --- | --- |
| 40 | Hexyl Acetate |
| 20 | Isoeugenyl Acetate |
| 50 | Aladinate ®[1)] |
| 1000 | Hexylcinnamic Aldehyde |
| 400 | Bergamote oil |
| 10 | Ethyl Caproate |
| 50 | Cetalox ®[2)] |
| 50 | Raspberry ketone |
| 40 | Cis Jasmone |
| 20 | Cis-3-Hexenol |
| 300 | Coranol ™[3)] |
| 10 | Cyclogalbanate[4)] |
| 400 | (1'R,E)-2-ethyl-4-(2',2',3'-trimethyl-3'-cyclopenten-1'-yl)-2-buten-1-ol |
| 20 | Delta Damascone |
| 500 | Dihydromyrcenol |
| 140 | Floralozone ®[5)] |
| 80 | Gamma Undecalactone |
| 1300 | Habanolide ®[6)] |
| 1700 | Hedione ®[7)] |
| 40 | Heliopropanal[8)] |
| 20 | Heliotropine[9)] |
| 200 | Ionone Beta |
| 750 | Iso E ® Super[10)] |
| 450 | Phenoxy Isobutyrate |
| 20 | Isoeugenol Extra |
| 500 | Isoraldeine ®[11)] |
| 100 | Lyral ®[12)] |
| 50 | 10%* 2,6-dimethyl-5-heptanal |
| 40 | Methylbutyrate 2 Ethyle |
| 100 | Muscenone Delta[13)] |
| 100 | Polysantol ®[14)] |
| 400 | Salicynile ®[15)] |
| 20 | Triplal ®[16)] |
| 300 | Undecavertol ®[17)] |
| 80 | 10%* Vanilline |
| 9300 | |

*in dipropyleneglycol
**in isopropyle myristate
[1)]3-methyl-2-hexenyl acetate; origin: Firmenich SA, Geneva, Switzerland
[2)]dodecahydro-3a,6,6,9a-tetramethyl-naphtho[2,1-b]furan; origin: Firmenich SA, Geneva, Switzerland
[3)]4-cyclohexyl-2-methyl-2-butanol; origin: Firmenich SA, Geneva, Switzerland
[4)](cyclohexyloxy)-acetate d'allyle; origin: Symrise, Holzminden, Allemagne
[5)]3-(4/2-ethylphenyl)-2,2-dimethylpropanal; origin: International Flavors & Fragrances, USA
[6)]pentadecenolide; origin: Firmenich SA, Geneva, Switzerland
[7)]methyl dihydrojasmonate; origin: Firmenich SA, Geneva, Switzerland
[8)]3-(1,3-benzodioxol-5-yl)-2-methylpropanal; origin: Firmenich SA, Geneva, Switzerland
[9)]1,3-benzodioxole-5-carbaldehyde; origin: Firmenich SA, Geneva, Switzerland
[10)]1-(octahydro-2,3,8,8-tetramethyl-2-naphthalenyl)-1-ethanone; origin: International Flavors & Fragrances, USA
[11)]3-methyl-4-(2,6,6-trimethyl-2cyclohexen-1-yl)-3-buten-2-one, origin: Givaudan SA, Vernier, Switzerland
[12)]4/3-(4-hydroxy-4-methylpentyl)-3-cyclohexene-1-carbaldehyde; origin: International Flavors & Fragrances, USA
[13)]3-methyl-5-cyclopentadecen-1-one; origin: Firmenich SA, Geneva, Switzerland
[14)]3,3-dimethyl-5-(2,2,3-trimethyl-3-cyclopenten-1-yl)-4-penten-2-ol; origin: Firmenich SA, Geneva, Switzerland
[15)](2Z)-2-phenyl-2-hexenitrile; origin: Firmenich SA, Geneva, Switzerland
[16)]2,4-dimethyl-3-cyclohexene-1-carbaldehyde; origin: Firmenich SA, Geneva, Switzerland
[17)]4-methyl-3-decen-5-ol; origin: Givaudan SA, Vernier, Switzerland The addition of 700 parts by weight of 4-methyl-6-phenylhexan-2-ol to the above-described composition imparted to the latter green and gardenia/lily of the valley connotation and boosted the violet of the original composition.

What is claimed is:

1. A perfuming composition comprising:
   i) at least one compound of formula (I),

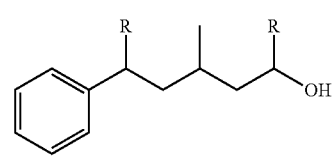

(I)

in the form of any one of its stereoisomers or a mixture thereof and wherein one R represents a methyl group and the other R is a hydrogen atom;
   ii) at least one ingredient selected from the group consisting of a perfumery carrier and a perfumery base; and
   iii) optionally at least one perfumery adjuvant, wherein the compound of formula (I) is present in an amount sufficient to impart lily of the valley/gardenia odor notes to the composition.

2. The perfuming composition of claim 1, wherein the compound of formula (I) comprises 4-methyl-6-phenyl-hexan-2-ol.

3. The perfuming composition of claim 1, wherein the compound of formula (I) is (2RS,4RS)-4-methyl-6-phenyl-hexan-2-ol.

4. A consumer product that includes at least one compound of formula (I),

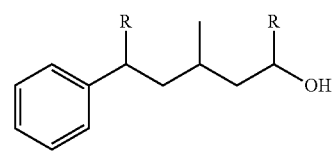

(I)

in the form of any one of its stereoisomers or a mixture thereof, wherein one R represents a methyl group and the other R is a hydrogen atom, and wherein the compound of formula (I) is present in an amount sufficient to impart lily of the valley/gardenia odor notes to the consumer product.

5. The consumer product of claim 4, wherein the compound of formula (I) comprises 4-methyl-6-phenylhexan-2-ol.

6. The consumer product of claim 4, wherein the compound of formula (I) is (2RS,4RS)-4-methyl-6-phenyl-hexan-2-ol.

7. The consumer product of claim 4, which is a perfume, a fabric care product, a body-care product, an air care product or a home care product.

8. The consumer product of claim 4, which is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

* * * * *